United States Patent

Van Antwerp et al.

[11] Patent Number: 5,257,980
[45] Date of Patent: Nov. 2, 1993

[54] SUBCUTANEOUS INJECTION SET WITH CRIMP-FREE SOFT CANNULA

[75] Inventors: William P. Van Antwerp, Los Angeles; Todd Kinsfather, Valencia; Jeffery Van Funderburk, Granada Hills; Deborah C. McIntyre, Agoura, all of Calif.

[73] Assignee: MiniMed Technologies, Ltd., Sylmar, Calif.

[21] Appl. No.: 42,969

[22] Filed: Apr. 5, 1993

[51] Int. Cl.$^5$ .............................................. A61M 5/00
[52] U.S. Cl. ................................. 604/282; 604/165
[58] Field of Search .............. 604/165, 283, 282, 164, 604/158

[56] References Cited

U.S. PATENT DOCUMENTS

| | | | |
|---|---|---|---|
| 4,755,649 | 7/1988 | Barker et al. | 604/283 |
| 4,762,517 | 8/1988 | McIntyre et al. | 604/283 |
| 4,863,442 | 9/1989 | DeMello et al. | 604/282 |
| 4,955,863 | 9/1990 | Walker et al. | 604/164 |
| 4,966,588 | 10/1990 | Rayman et al. | 604/283 |
| 4,978,334 | 12/1990 | Toye et al. | 604/164 |
| 5,176,602 | 1/1993 | Bartholomew et al. | 604/164 |

Primary Examiner—Paul J. Hirsch
Attorney, Agent, or Firm—Leslie S. Miller; Stuart O. Lowry

[57] ABSTRACT

A device for use as a subcutaneous injection set is disclosed which has a soft cannula through which a selected medication can be administered to a patient, wherein the soft cannula is adapted for transcutaneous placement by an insertion needle substantially without crimping or kinking. The cannula is supported by and protrudes outwardly from a housing adapted to receive the selected medication. The insertion needle is initially inserted through a septum on the housing and further through the cannula to provide a rigid structure to insert the soft cannula through the patient's skin. The insertion needle and cannula are constructed to prevent longitudinal slippage of the cannula on the needle during the insertion process, thereby preventing undesired crimping or kinking of the soft cannula. After insertion, the needle is withdrawn from the cannula and housing to permit medication delivery to the patient.

21 Claims, 2 Drawing Sheets

SUBCUTANEOUS INJECTION SET WITH CRIMP-FREE SOFT CANNULA

BACKGROUND OF THE INVENTION

1. Field of the Invention

The present invention relates generally to injection devices for use with an external infusion system for subcutaneous delivery of a selected medication or other therapeutic fluid to a patient, and more particularly to an improved subcutaneous injection set of the type having a soft or flexible cannula, in combination with means for reducing and/or eliminating undesired crimping or kinking of the soft cannula during transcutaneous placement.

Subcutaneous injection devices are generally known in the art for use in the administration of a selected medication or other therapeutic fluid to a desired subcutaneous site located beneath the skin of a patient. Such injection devices or sets commonly include a tubular cannula or catheter which is supported by and protrudes from a compact housing adapted to receive the infusion fluid via a delivery to be connected suitably to other components of the fluid infusion system.

An insertion needle is normally provided to extend through a lumen formed in the cannula and thereby provide a rigid backstop structure having a sharp-tipped end to facilitate transcutaneous placement of the cannula. The insertion needle is thereafter withdrawn to leave the cannula in place for subcutaneous fluid infusion to the patient. A preferred subcutaneous injection set of this general type is described and claimed in U.S. Pat. No. 4,755,173, to Konopka et al., and in U.S. Pat. No. 5,176,662, to Bartholomew et al., both of which are hereby incorporated herein by reference.

For optimum patient comfort during use, the cannula is desirably constructed with a high degree of softness and flexibility. However, a soft and flexible cannula can on occasion become crimped or kinked during the insertion process, resulting in obstruction of the lumen of the cannula and resultant inability to deliver the desired medication to the patient. More specifically, during the transcutaneous insertion step, substantial longitudinal force is applied to the cannula as the insertion needle is passed through the patient's skin.

This longitudinal force can sometimes cause the soft cannula to displace or slip longitudinally on the insertion needle, resulting in incomplete cannula insertion and sufficient kinking to obstruct the lumen of the cannula. In the past, this problem has been addressed primarily by increasing the stiffness of the cannula, by means of increased wall thickness or variations in the cannula material to resist crimping during the insertion step. Unfortunately, these prior approaches effectively reduce the softness and flexibility of the cannula, and thereby compromise patient comfort.

There exists, therefore, a significant need for further improvements in subcutaneous injection sets and the like, particularly with respect to providing a cannula with a high degree of softness and flexibility, and wherein the soft cannula can be transcutaneously placed in a reliable manner substantially without crimping or kinking. The present invention fulfills these needs and provides further related advantages without incurring any substantial relative disadvantage.

SUMMARY OF THE INVENTION

The disadvantages and limitations of the background art discussed above are overcome by the present invention. In accordance with the invention, a subcutaneous injection set includes a soft cannula for transcutaneous placement through the skin of a patient by means of an insertion needle, wherein the soft cannula and insertion needle include means for substantially minimizing or eliminating cannula crimping or kinking during the insertion step. The insertion needle is removable from the cannula, subsequent to the insertion step, whereby the cannula provides a transcutaneous path or lumen through which a selected medication or other therapeutic fluid can be infused to the patient.

In the preferred form, the subcutaneous injection set is constructed generally in accordance with the above-incorporated by reference U.S. Pat. No. 4,755,173 and U.S. Pat. No. 5,176,662. More specifically, the soft cannula protrudes from a compact housing having an internal chamber for receiving the selected medication or other infusion fluid via a delivery tube or the like, with the infusion fluid passing from the housing chamber through the lumen of the cannula to the patient.

The insertion needle is initially received through the housing and through the lumen of the cannula to facilitate transcutaneous cannula placement after which the insertion needle is withdrawn from the injection set. The cannula is constructed from a soft and flexible polymeric material to provide a high degree of patient comfort during use.

A mechanism is provided for controlling friction between the insertion needle and cannula during the insertion step, and thereby prevent and substantially eliminate occurrence of cannula crimping. In one preferred form, said friction control means comprises a roughened surface formed on the exterior of the insertion needle, as by grit blasting, such that the coefficient of friction between the insertion needle and cannula is sufficient to prevent cannula slippage in response to longitudinal forces applied to the cannula during the insertion step.

In another alternative and preferred form of manufacturing the cannula, the cannula may be heat formed around a grit-blasted surface, thus increasing the coefficient of friction.

In other alternative and preferred forms of the invention, a small radial step can be formed in the insertion needle at a position disposed within the cannula generally at or adjacent to the distal end of the cannula. The step comprises a reduction in the diametric cross-sectional size of the insertion needle, with the cannula being formed snugly thereon, whereby the needle step defines a small shoulder which obstructs longitudinal displacement of the cannula on the insertion needle during the insertion step.

In another form, the coefficient of friction between the insertion needle and cannula is increased by coextruding the cannula with an internal spiral filament which applies a radially inward force to the insertion needle, when said needle is received through the lumen of the cannula. In another alternative preferred form, the distal end of the cannula may be temporarily affixed or locked to the exterior of the insertion needle by a water soluble adhesive or the like, wherein the adhesive prevents relative displacement between the cannula and needle during the insertion step but thereafter rapidly dissolves to permit unobstructed withdrawal of the insertion needle.

In each of the preferred forms of the invention, subsequent to the insertion step, the insertion needle is withdrawable from the cannula quickly and easily, and without significant risk of cannula kinking or crimping. The patient's tissue tends to support the cannula in a secure and stable manner, to permit withdrawal of the insertion needle.

Other features and advantages of the present invention will become more apparent from the following detailed description, taken in conjunction with the accompanying drawings which illustrate, by way of example, the principles of the invention.

DESCRIPTION OF THE DRAWINGS

These and other advantages of the present invention are best understood with reference to the drawings, in which.

DETAILED DESCRIPTION OF THE PREFERRED EMBODIMENT

Figure 1:
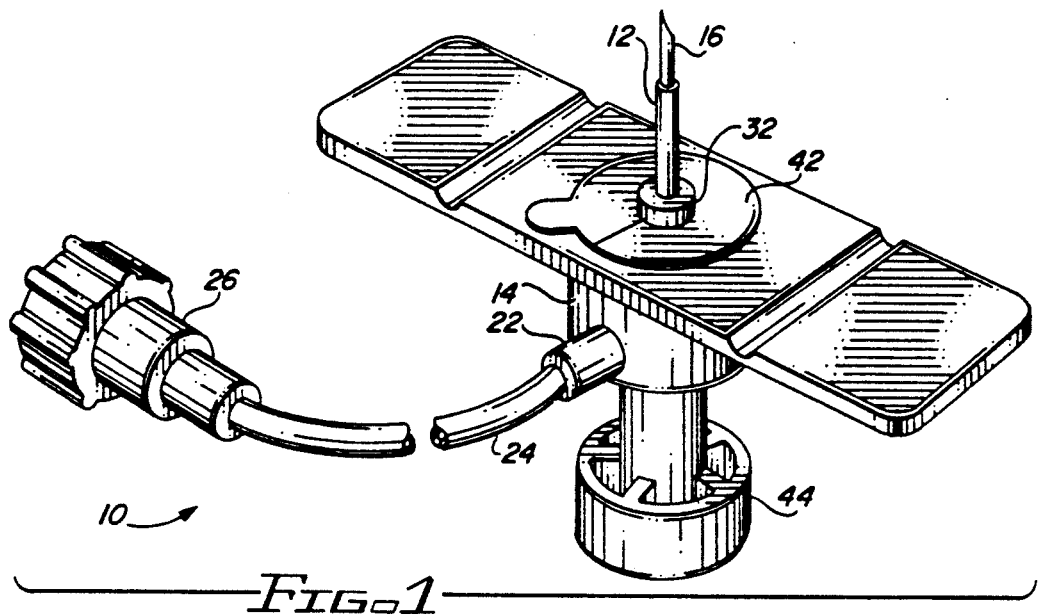
FIG. 1 is a perspective view illustrating a subcutaneous injection set embodying the novel features of the invention.

As shown in the exemplary drawings, an improved subcutaneous injection set referred to generally in FIG. 1 by the reference numeral 10 is provided for subcutaneous delivery of a selected medication or other therapeutic infusion fluid to a patient. The injection set 10 includes a tubular cannula 12 supported by a compact housing 14 to which the medication is supplied, wherein the cannula 12 is constructed with a high degree of softness and/or flexibility to enhance patient comfort during use.

The cannula 12 is carried on an insertion needle 16 used to insert the cannula through the skin 18 (FIGS. 2 and 3) of a patient. In accordance with the invention, means are provided to prevent kinking or crimping of the soft cannula 12 on the insertion needle 16 during the transcutaneous placement step.

Figure 2:
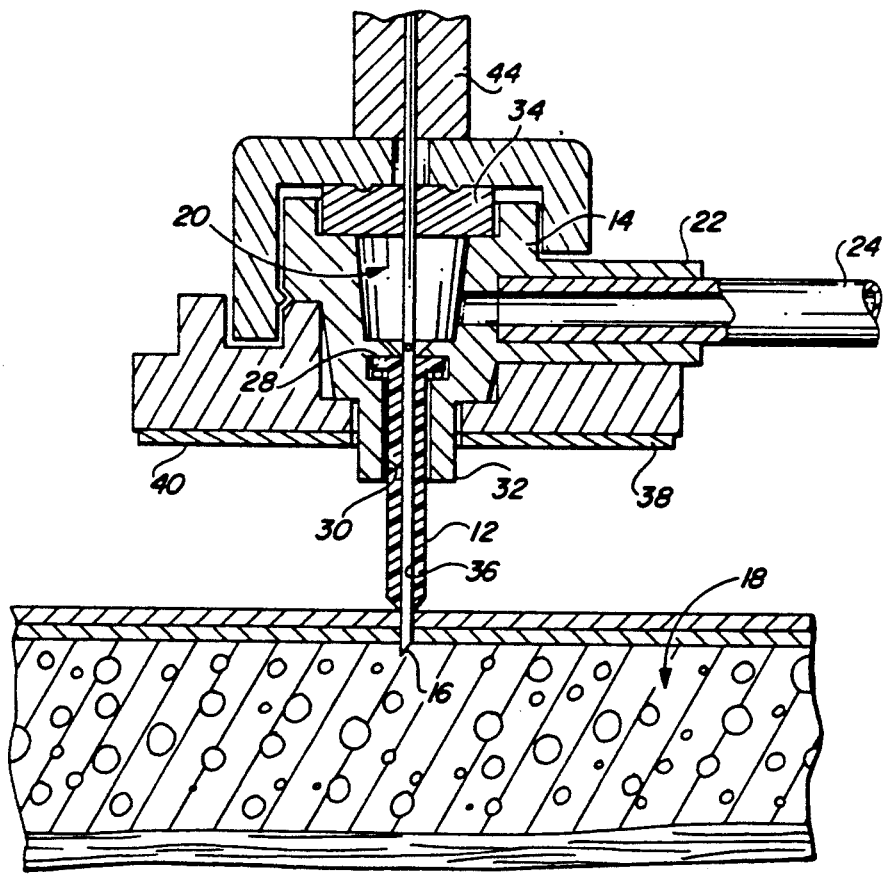
FIG. 2 is an enlarged fragmented sectional view illustrating an insertion step for transcutaneous placement of a cannula.
Figure 3:
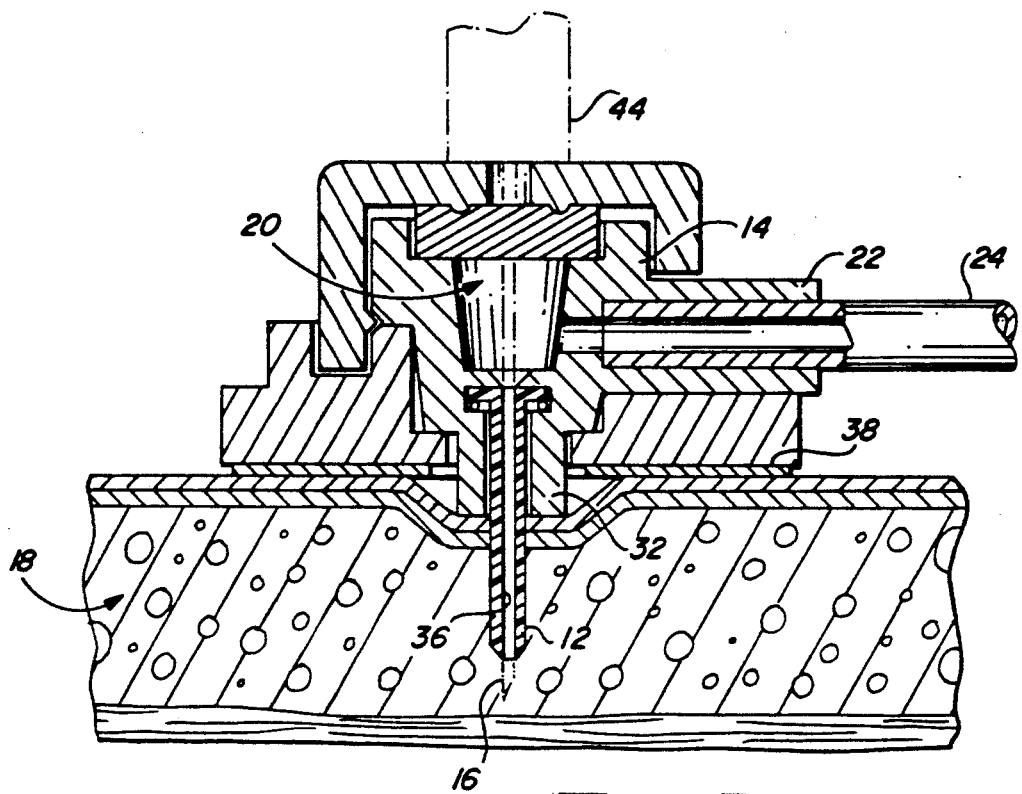
FIG. 3 is an enlarged fragmented sectional view similar to FIG. 2, but illustrating the cannula in position for fluid infusion to the patient.

The subcutaneous injection set 10 shown in FIGS. 1-3 is constructed generally in accordance with the injection set described and claimed in the above-incorporated by reference U.S. Pat. No. 4,755,173 and U.S. Pat. No. 5,176,662. More particularly, the injection set 10 includes the housing 14 which is preferably constructed from a lightweight molded plastic or the like to include an internal chamber 20 and a side port or fitting 22 adapted for connection to a medication delivery tube 24. The medication or other selected fluid is supplied from the components, (not shown) of an external fluid infusion system through a standard luer connection 26 and further through the delivery tube 24 to the chamber 20 within the housing 14.

The soft cannula 12, in the preferred form, is constructed from a selected fluoropolymer such as fluorinated ethylene polymer (FEP), or a fluoropolymer-based material to include a flanged base end 28 supported at the inboard end of a bore 30 formed in a support hub 32 protruding outwardly from the housing 14. From the base end 28, the cannula 12 protrudes through and beyond the hub bore 30, terminating in a leading or distal end adapted for placement at a selected subcutaneous injection site within a patient.

The insertion needle 16, formed typically from a medical grade stainless steel, is initially mounted to extend through a resilient, self-sealing septum 34 on the housing 14. The insertion needle extends through the housing chamber 20 and further through a hollow lumen 36 defined by the cannula 12, terminating in a sharp or pointed distal end disposed at least a short distance beyond the corresponding distal end of the cannula.

In use, as described in U.S. Pat. No. 4,755,173 and in U.S. Pat. No. 5,176,662, the cannula 12 is placed transcutaneously at a selected fluid injection site on the patient's skin 18 by piercing the skin with the insertion needle 16 to simultaneously position the needle and cannula transcutaneously. In this regard, the distal end of the cannula 12 is normally shaped to define a tapered bevel, as shown best in FIGS. 2 and 3, to facilitate needle-guided entry into and through the patient's skin.

A holding pad 38 is desirably positioned at an underside of the housing 14 and includes an adhesive film 40 exposed upon removal of a peel-off strip 42 to releasable retain the entire injection set at the desired position on the patient's skin. When proper transcutaneous cannula placement is obtained, the insertion needle 16 is withdrawn by means of a manually accessible handle 44, thereby leaving the cannula in place with its lumen 36 defining an open path for subcutaneous fluid infusion to the patient.

In accordance with the present invention, the insertion needle 16 and soft cannula 12 are designed to prevent or resist undesired kinking or crimping of the cannula 12 in response to longitudinal forces applied thereto in the course of transcutaneous placement. In other words, means are provided to prevent longitudinal displacement or slippage of the soft cannula on the insertion needle 16, during the insertion step. Such slippage, if it occurs, essentially causes the cannula to twist and deform into an accordion-like configuration on the needle 16, particularly at the externally unsupported portion of the cannula disposed between the hub 30 and the point of entry into the patient's skin.

Figure 4:
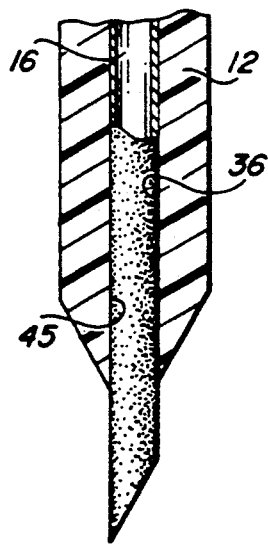
FIG. 4 is an enlarged fragmented sectional view illustrating the cannula and accompanying insertion needle in accordance with one preferred form of the invention.

More specifically, in one preferred form as viewed in FIG. 4, friction means are provided to act between the outer diameter surface of the insertion needle 16 and the inner diameter of the cannula 12, to prevent cannula slippage on the insertion needle during the insertion step. Such friction means comprises formation of the needle 16 to include a roughened exterior surface 45 for purposes of increasing the coefficient of friction between the needle 16 and the cannula 12, sufficiently to prevent cannula crimping or kinking.

The roughened exterior surface 45 on the insertion needle 16 is obtained quickly and easily by subjecting the exterior of the insertion needle 16 to a grit blasting step, such as by grit blasting the needle with alumina particles having a particle size on the order of about 50-150 micron, for a brief period of about thirty seconds. Such grit blasted surface 45 on the exterior of the insertion needle has been found to result in dramatic reduction and substantial elimination of cannula crimping or kinking, in an FEP or fluoropolymer-based cannula having a wall thickness of about 4 mils.

Figure 5:
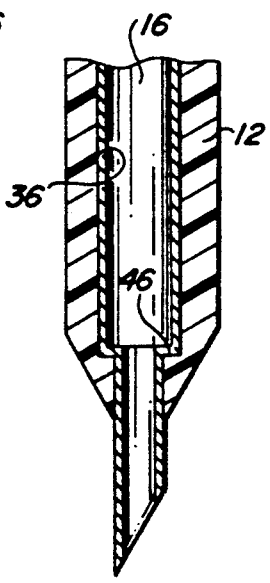
FIG. 5 is an enlarged fragmented sectional view similar to FIG. 5, but illustrating an alternative preferred form of the invention.

FIG. 5 illustrates an alternative preferred form of the invention, wherein the coefficient of friction between the insertion needle and cannula is increased during the insertion step by providing a step 46 along the needle 16, at a location generally within the beveled distal end of the cannula 12. In particular, the step 46 comprises a slight reduction in the cross sectional size of the needle 16, such that the pointed tip end of the needle has a slightly reduced cross sectional size in relation to the remainder of the needle.

The step 46 thus defines an outwardly presented shoulder. The beveled leading edge on the cannula 12 is normally formed by a heat and pressure shaping formation step, such that the interior lumen 36 of the cannula is shaped at the distal end to conform with the shape of the needle step 46. With this configuration, the needle step 46 effectively locks the distal or leading end of the cannula against upward slippage on the needle during the insertion step, and thereby prevents undesired cannula crimping or kinking.

Figure 6:
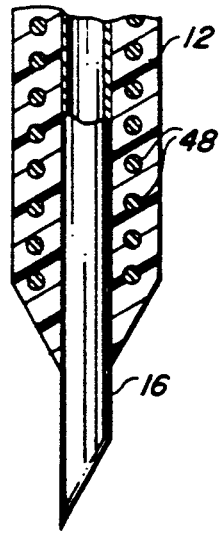
FIG. 6 is an enlarged fragmented sectional view similar to FIGS. 4 and 5, and showing a further alternative embodiment of the invention.

A further alternative embodiment is shown in FIG. 6, wherein the coefficient of friction between the cannula and the needle is increased by forming the cannula 12 with a spiral wound filament 48 coextruded therein. The normal unstressed cross sectional size of the thus-formed cannula is slightly less than the outer diameter size of the insertion needle 16, whereby the filament 48 functions to apply a radially inward compression force to the needle, when the insertion needle is received through the catheter lumen.

Appropriate design of the filament 48 and related cannula/needle geometries will effectively increase the coefficient of friction sufficient to prevent cannula crimping or kinking during the insertion step. A variety of materials may be used for the filament 48, including, for example, carbon fiber, various polymeric fibers such as those known by the trademarks ARAMID and KEVLAR, titanium wire, etc.

Figure 7:
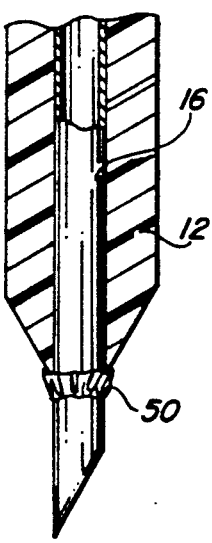
FIG. 7 is an enlarged fragmented sectional view illustrating a still further alternative embodiment of the present invention.

FIG. 7 shows a further alternative embodiment of the invention, wherein the coefficient of friction acting between the cannula 12 and the insertion needle 16 is increased during the insertion step by effectively locking the distal end of the cannula 12 on to the needle with an adhesive material 50. The adhesive 50 comprises a bead of a water soluble material, such as polyvinyl alcohol, and functions to lock the cannula against longitudinal displacement on the needle and resultant crimping or kinking during the insertion step. However, the adhesive 50 dissolves quickly in the presence of body fluids, thereby releasing or unlocking the needle 16 within a short period following transcutaneous placement, to permit easy subsequent removal of the needle from the cannula 12.

In all of the various forms of the invention as described above, the soft cannula 12 is thus effectively retained against crimping or kinking during the insertion step. The cannula 12 is retained against longitudinal slippage on the needle 12, thereby assuring positive cannula transcutaneous placement with the lumen 36 defining an uninterrupted fluid infusion path. When insertion is achieved in each embodiment, the needle 16 can be withdrawn quickly and easily without risk of cannula crimping. In this regard, the inserted cannula is structurally supported by the patient's skin and subcutaneous tissue, wherein this structural support functions to retain the cannula firmly and securely in place as the insertion needle is withdrawn.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A subcutaneous injection set, comprising:
    housing means defining an internal chamber adapted for receiving a selected infusion fluid, said housing means further defining an outlet bore;
    a soft cannula mounted generally within said outlet bore and protruding outwardly from said housing, said cannula defining a hollow lumen;
    an insertion needle removably received through said housing chamber and further through said cannula lumen and terminating in a point tip disposed at least slightly beyond said cannula, said insertion needle being withdrawable from said cannula and from said housing subsequent to transcutaneous placement of said cannula through the skin of a patient; and
    means for preventing slippage of said cannula in a direction longitudinally along said insertion needle during transcutaneous placement thereof to correspondingly prevent cannula crimping.

2. A subcutaneous injection set as defined in claim 1, wherein said slippage preventing means comprises:
    friction means coacting between an inner diameter surface of said cannula lumen and an outer diameter surface of said needle.

3. A subcutaneous injection set as defined in claim 2, wherein said friction means comprises:
    a grit blasted outer diameter surface on said needle.

4. A subcutaneous injection set as defined in claim 2, wherein said friction means further comprises:
    a non-smooth surface formed on said inner diameter surface of said cannula.

5. A subcutaneous injection set as defined in claim 2, wherein said friction means comprises:
    a spiral wound filament formed within said cannula whereby said filament applies a radially inward compression force to said needle when said needle is received through said lumen.

6. A subcutaneous injection set as defined in claim 2, wherein said friction means comprises:
    a step formed on said needle at a position disposed generally within a distal end of said catheter, said catheter being formed to conform with the shape of said step.

7. A subcutaneous injection set as defined in claim 1, wherein said slippage preventing means comprise:
    means for releasably locking a distal end of said cannula on said needle during transcutaneous placement thereof.

8. A subcutaneous injection set as defined in claim 7, wherein said locking means comprises:
  a step formed on said needle at a position disposed generally within a distal end of said catheter, said catheter being formed to conform with the shape of said step.

9. A subcutaneous injection set as defined in claim 7, wherein said locking means comprises:
  a soluble adhesive for locking said cannula distal end on said needle during transcutaneous placement thereof, said adhesive dissolving in the presence of body fluids to release said needle from said cannula.

10. A subcutaneous injection set as defined in claim 1, wherein said cannula is made from a fluoropolymer.

11. A subcutaneous injection set as defined in claim 10, wherein said cannula is made from fluorinated ethylene polymer (FEP), 12. In a transcutaneous medical fluid infusion device having a soft cannula defining a hollow lumen and an insertion needle extending through said cannula with a pointed tip disposed at least slightly beyond a distal end of the cannula, wherein the needle provides a rigid backstop structure for transcutaneous cannula placement and is thereafter withdrawable from the cannula to permit medical fluid infusion through said lumen, the improvement comprising:
  means for preventing slippage of said cannula in a direction longitudinally along said insertion needle during transcutaneous placement thereof to correspondingly prevent cannula crimping.

13. A transcutaneous medical fluid infusion device as defined in claim 12, wherein said slippage preventing means comprises:
  friction means coacting between an inner diameter surface of said cannula lumen and an outer diameter surface of said needle.

14. A transcutaneous medical fluid infusion device as defined in claim 13, wherein said friction means comprises:
  a grit blasted outer diameter surface on said needle.

15. A subcutaneous injection set as defined in claim 13, wherein said friction means further comprises:
  a non-smooth surface formed on said inner diameter surface of said cannula.

16. A transcutaneous medical fluid infusion device as defined in claim 13, wherein said friction means comprises:
  a spiral wound filament formed within said cannula whereby said filament applies a radially inward compression force to said needle when said needle is received through said lumen.

17. A transcutaneous medical fluid infusion device as defined in claim 13, wherein said friction means comprises:
  a step formed on said needle at a position disposed generally within a distal end of said catheter, said catheter being formed to conform with the shape of said step.

18. A transcutaneous medical fluid infusion device as defined in claim 12, wherein said slippage preventing means comprise:
  means for releasably locking a distal end of said cannula on said needle during transcutaneous placement thereof.

19. A transcutaneous medical fluid infusion device as defined in claim 18, wherein said locking means comprises:
  a step formed on said needle at a position disposed generally within a distal end of said catheter, said catheter being formed to conform with the shape of said step.

20. A transcutaneous medical fluid infusion device as defined in claim 18 wherein said locking means comprises:
  a soluble adhesive for locking said cannula distal end on said needle during transcutaneous placement thereof, said adhesive dissolving in the presence of body fluids to release said needle from said cannula.

21. A method of making a subcutaneous injection set, comprising:
  defining an internal chamber in a housing means, said internal chamber being adapted for receiving a selected infusion fluid;
  defining an outlet bore in said housing means;
  mounting a soft cannula generally within said outlet bore, said soft cannula protruding outwardly from said housing, said soft cannula defining a hollow lumen therein;
  removably placing an insertion needle through said housing chamber and further through said cannula lumen, said insertion needle terminating in a point tip disposed at least slightly beyond said cannula, said insertion needle being withdrawable from said cannula and from said housing subsequent to transcutaneous placement of said cannula through the skin of a patient; and
  providing means for preventing slippage of said cannula in a direction longitudinally along said insertion needle during transcutaneous placement thereof to correspondingly prevent cannula crimping.

* * * * *